US008146407B2

(12) United States Patent
Atchley et al.

(10) Patent No.: US 8,146,407 B2
(45) Date of Patent: Apr. 3, 2012

(54) PARTICLE COUNTER WITH ELECTRONIC DETECTION OF APERTURE BLOCKAGE

(75) Inventors: Peter Atchley, Northfield, MA (US); Scott D'Amron, Coral Springs, FL (US)

(73) Assignee: Beckman Coulter, Inc., Brea, CA (US)

( * ) Notice: Subject to any disclaimer, the term of this patent is extended or adjusted under 35 U.S.C. 154(b) by 532 days.

(21) Appl. No.: 12/487,448

(22) Filed: Jun. 18, 2009

(65) Prior Publication Data
US 2009/0315533 A1 Dec. 24, 2009

Related U.S. Application Data

(60) Provisional application No. 61/074,520, filed on Jun. 20, 2008.

(51) Int. Cl.
*G01N 15/06* (2006.01)
*G01N 15/00* (2006.01)
(52) U.S. Cl. .................. 73/61.71; 73/865.5
(58) Field of Classification Search ............ 73/61.71, 73/61.73, 865.5
See application file for complete search history.

(56) References Cited

U.S. PATENT DOCUMENTS

| | | | |
|---|---|---|---|
| 3,259,891 A | 7/1966 | Coulter et al. | |
| 3,444,463 A | 5/1969 | Coulter et al. | |
| 3,882,385 A | 5/1975 | Coulter et al. | |
| 3,963,984 A | 6/1976 | Coulter | |
| 4,078,211 A | 3/1978 | Longman, Jr. | |
| 4,307,339 A | 12/1981 | Ferrell | |
| 4,412,175 A | 10/1983 | Maynarez | |
| 4,450,435 A | 5/1984 | James | |
| 4,631,483 A | 12/1986 | Proni et al. | |
| 4,775,833 A | 10/1988 | Roos et al. | |
| 4,977,517 A | 12/1990 | Gibbs, Jr. et al. | |
| 6,389,912 B1 | 5/2002 | Wood | |
| 2007/0143033 A1* | 6/2007 | Zhang et al. ............ 702/26 |
| 2008/0286751 A1* | 11/2008 | Renaud et al. ............ 435/5 |

FOREIGN PATENT DOCUMENTS

GB      2 337 583 A     11/1999
WO   WO-2007/033669 A1  3/2007

OTHER PUBLICATIONS

International Search Report and Written Opinion for Application No. PCT/US2009/047917 dated Sep. 21, 2009.

* cited by examiner

*Primary Examiner* — Hezron E Williams
*Assistant Examiner* — Jamar Ray
(74) *Attorney, Agent, or Firm* — Merchant & Gould P.C.

(57) ABSTRACT

An apparatus for characterizing particles suspended in a liquid sample containing electrolyte including a sample chamber to hold the liquid sample and a collection chamber to hold an electrolyte solution. A wall separates the chambers and includes an aperture to allow passage of particles between the chambers; and a pair of electrodes are disposed on opposite sides of the aperture to induce a current through the aperture. A pressure source forces the sample to pass from the sample chamber into the collection chamber; and a processor measures a signal representative of electric resistance variation between the electrodes to enable determination of the size of the particle within the liquid passing through the aperture, wherein the processor is adapted to monitor two or more parameters characterizing the flow of particles through the aperture, and to detect a potential blockage of the aperture by detecting a change in any one of the parameters.

18 Claims, 8 Drawing Sheets

PARTICLE COUNTER WITH ELECTRONIC DETECTION OF APERTURE BLOCKAGE

CROSS-REFERENCE TO RELATED APPLICATIONS

This application claims the benefit of U.S. Provisional Application No. 61/074,520, filed Jun. 20, 2008, entitled "Particle Counter with Electric Detection of Aperture Blockage" and is entirely incorporated by reference herein.

TECHNICAL FIELD

The present disclosure generally relates to a particle characterization device and an automated method of detecting blockage in an aperture of said particle characterization device.

BACKGROUND

The Coulter principle, also known as electronic sensing zone technology, is a well established method of characterizing the size and number of particles in a liquid sample. According to the Coulter principle, particles can be characterized by their effect on a current-induced movement of electrolyte through a small aperture as the particle passes through the aperture. Entry of a particle into the aperture displaces some of the charged electrolyte in the aperture, causing an increased electrical resistance across the aperture, resulting in an increased voltage measured across the aperture when current is held constant. As the particle exits the aperture, normal flow of electrolyte through the aperture resumes, resulting in a return to the starting voltage across the aperture before the particle entered. In this way, passage of a single particle through the aperture is identified by a characteristic voltage pulse across the aperture. The height of this voltage pulse is generally dependent on the size of the particle, since a larger particle will displace more electrolyte in the aperture, resulting in a larger voltage difference when the particle enters and passes through the aperture.

A Coulter Counter® is a particle characterization device that uses the Coulter principle to determine the number and sizes of particles in a liquid sample. The counter device comprises two liquid-containing chambers separated by a wall, with an aperture in the wall that allows electrolyte and particles in the liquid of the chambers to move from one chamber to the other. A pair of electrodes connected to a power source and disposed across the aperture, one in each chamber, provides a voltage difference across the aperture. Electrolytes in the liquid move from one chamber to the other in response to the applied voltage, generating an electric current. An applied force, such as a vacuum or the movement of a piston, causes the liquid to move from one chamber to the other. A detector monitors the voltage across the aperture, and a processor analyzes the voltage changes as liquid, electrolyte, and particles pass through the aperture from one chamber to the other, identifying and characterizing individual particles based on the characteristic voltage variation as the particles pass through the aperture.

Coulter Counters® are commonly used to characterize the number and types of cells in a biological sample, determining, for example, the number of red blood cells, white blood cells, and platelets in a blood sample. A Coulter Counter® can also be used in non-biological applications, characterizing the number and size-distribution of particles dispersed in any suitable sample.

The size of the aperture in a Coulter Counter® is selected to be larger than the particles suspected of being present in the liquid, yet small enough so that generally particles pass through the aperture one at a time. During a particle-characterization run, it is possible for the aperture to become blocked, typically by sample particles in the liquid that are larger than the aperture, by foreign particles such as dust or debris in the liquid, by aggregates of sample particles in the liquid, or by multiple particles passing through the aperture at the same time. If the aperture becomes blocked during a run, the run must typically be stopped and the blockage removed before particle analysis can continue. There are currently several methods of identifying blockage of the aperture during a run. A magnified window focused on the aperture can allow visual identification of a blockage. Alternatively, a magnified image of the aperture, such as one created by a CCD device focused on the aperture, can be monitored during the run. Both these methods depend on the presence of a user to continuously monitor a run, with the disadvantage that it may be difficult to maintain an optical focus on the aperture, and blockage of the aperture may be difficult to see, whether through a window or in a CCD image.

Automated methods of identifying blockage in an aperture of a Coulter Counter® type particle characterization device have been disclosed. U.S. Pat. No. 4,412,175; U.S. Pat. No. 4,450,435; U.S. Pat. No. 4,775,833; U.S. Pat. No. 6,389,912; and WO 2007/033669 disclose methods of detecting aperture blockage based on the width of the voltage pulse associated with passage of a particle through the aperture. The voltage across the aperture increases as a particle enters, remains high as the particle passes through, then returns to the initial level as the particle exits the aperture. A particle that blocks the aperture, or one that becomes entrapped in the aperture, is prevented or delayed from exiting the aperture, causing a sustained higher voltage across the aperture characterized by an increased pulse-width. It may be difficult, however, for this method to detect a partial or transient blockage of the aperture, or to distinguish blockage from other factors affecting aperture voltage, such as the presence of air in the sample.

Therefore, a need exists for a more reliable, automated method of detecting blockage in the aperture of a Coulter Counter® type particle characterization device. The present disclosure addresses that need by providing a particle characterization device adapted to more reliably and automatically detect both partial and complete blockages of the aperture.

SUMMARY

The present disclosure provides a Coulter Counter® type particle characterization device adapted to reliably and automatically detect blockage of an aperture by establishing threshold values for multiple parameters associated with the characterization of particles during an analysis run. Each of these parameters is monitored during the run, and any measured parameter that exceeds a preselected threshold value indicates partial or complete blockage of the aperture. The multiple parameters can include, for example, flow rate, aperture resistance, count rate, and pulse concentration. The particle characterization device can be further adapted to automatically take a predetermined action when a blockage is detected, such as attempting to remove the blockage and then completing the analysis run without intervention by the user. The particle characterization device of the present disclosure has the advantage that a user is not required to visually monitor the aperture during the run, or be present to take corrective action if a blockage is detected. An advantage over previous automated blockage detection methods that rely on an analysis of a single parameter is that the analysis of multiple parameters associated with particle characterization provides a more reliable detection of aperture blockage, particularly partial blockage, and gives fewer false positives. A given aperture blockage may affect one parameter more than others. Such a blockage might be detected by one parameter but not by the others, and would therefore not be detected if the single parameter analyzed was not the one most affected by the blockage. That blockage, however, would be reliably detected by a device of the present disclosure, which detects a blockage if any of the parameters exceeds a threshold value, regardless of which parameter thresholds are exceeded and which are not.

In addition, the use of a combination of parameters to identify blockage allows the threshold value of each parameter to be set more conservatively, since a single parameter (single threshold value) is not relied on to identify all blockages. This provides a method that is both more reliable in detecting a blockage (by the analysis of multiple parameters), yet is less likely to incorrectly identify a blockage (since more conservative threshold values can be used). The use of multiple parameters is especially advantageous in detecting a partial blockage of an aperture, where the effect on any single parameter is usually less, and the effect is typically less predictable.

In one aspect, an apparatus for characterizing particles suspended in a liquid sample containing electrolyte is disclosed, the apparatus includes: (a) a sample chamber for holding the liquid sample and a collection chamber for holding an electrolyte solution, the sample and collection chambers separated by a wall; (b) an aperture in the wall for passage of particles between the sample chamber and collection chamber; (c) a pair of electrodes disposed on opposite sides of the aperture for inducing an electric current through the aperture; (d) a pressure source for drawing the liquid sample from the sample chamber into the collection chamber through the aperture; and (e) a processor for measuring a signal representative of electrical resistance variation between the electrodes to enable determination of the size of the a particle within the liquid passing through the aperture, wherein the processor is adapted to detect a potential blockage of the aperture by detecting a predetermined change in one or more parameters characterizing the flow of particles through the aperture, wherein at least one of the one or more parameters is selected from the group consisting of flow rate, count rate, pulse concentration, and steady-state aperture resistance.

In a second aspect, the apparatus of the first aspect includes the predetermined change being a measured value that exceeds a predetermined threshold value for any of the one or more parameters, and wherein the predetermined threshold value is a value that is predetermined by a user of the apparatus.

In a third aspect, the apparatus of either the first or second aspects includes the predetermined change being a measured value that exceeds a predetermined threshold value for any of the one or more parameters, and wherein the predetermined threshold value for at least one of the one or more parameters is a relative value dependant on a measured value from a previous particle characterization run.

In a fourth aspect, the apparatus of any one of the first to third aspects includes the predetermined change being a measured value that exceeds a predetermined threshold value for any of the one or more parameters, and wherein the predetermined threshold value for at least one of the one or more parameters is a relative value dependant on a measured value from the present particle characterization run.

In a fifth aspect, the apparatus of any one of the first to fourth aspects includes the predetermined change being a measured value that exceeds a predetermined threshold value for a predetermined length of time.

In a sixth aspect, the apparatus of any one of the first to fifth aspects includes the processor being further adapted to direct a preselected action when potential blockage of the aperture is detected, wherein the preselected action is preselected by a user of the apparatus from a choice of two or more actions.

In a seventh aspect, the apparatus of any one of the first to sixth aspects includes the processor adapted to detect a potential blockage of the aperture during a particle characterization run by detecting a predetermined change in the flow rate through the aperture, wherein the predetermined change is a measured flow rate that is approximately 60% or less of the flow rate measured at the beginning of the particle characterization run.

In an eighth aspect, the apparatus of any one of the first to seventh aspects includes the processor adapted to simultaneously monitor flow rate through the aperture and steady-state resistance across the aperture.

In a ninth aspect, the apparatus of any one of the first to seventh aspects includes the processor adapted to simultaneously monitor flow rate, count rate, pulse concentration, and steady-state resistance across the aperture.

In a tenth aspect, the apparatus of any one of the first to ninth aspects includes the processor adapted to monitor steady-state resistance across the aperture, and wherein the processor is adapted to detect a potential blockage of the aperture by detecting a change in the steady-state resistance across the aperture that leads to a change in voltage across the aperture of approximately 1 volt or more.

In an eleventh aspect, the apparatus of any one of the first to tenth aspects includes the processor adapted to monitor particle count rate during a particle characterization run, and wherein the processor is adapted to detect a potential blockage of the aperture by detecting a measured particle count rate during the run that is approximately 60% or less of the particle count rate measured during the beginning of the run.

In a twelfth aspect, a method for automatically detecting a potential blockage in an aperture of a Coulter-type particle-characterization device, the method embodied in a set of machine-readable instructions executed on a processor, includes: (a) monitoring one or more parameters characterizing the flow of particles through the aperture, wherein at least one of the one or more parameters is selected from the group consisting of flow rate, count rate, pulse concentration, and steady-state aperture resistance; (b) detecting a predetermined change in one of the one or more parameters, wherein the predetermined change is a measured value that exceeds a predetermined threshold value indicative of a blockage of the aperture; (c) identifying a potential blockage of the aperture when the measured value exceeds the predetermined threshold value; and (d) taking a predetermined action when a potential blockage of the aperture is identified.

In a thirteenth aspect, the method of the twelfth aspect includes the predetermined action of (d) being preselected by a user of the apparatus from a choice of two or more actions.

In a fourteenth aspect, the apparatus of either the twelfth or thirteenth aspects includes the steady state resistance across the aperture monitored in (a), and wherein a potential blockage of the aperture is identified in (c) when the measured steady-state resistance across the aperture exceeds a preselected percentage of the measured steady-state resistance across the aperture from the beginning of the particle characterization run.

DETAILED DESCRIPTION

The present disclosure provides a Coulter Counter® type device for characterizing particles suspended in a liquid sample, the device adapted to electronically detect blockage of an aperture during the characterization of particles passing through the aperture. The device is adapted to analyze multiple parameters characterizing passage of particles through the aperture, including liquid flow rate, aperture voltage, measured count rate, and measured concentration. Upper or lower threshold values for each parameter can be set prior to the start of a run. A potential blockage of the aperture is detected when any of the measured values exceeds the set threshold value. The Coulter Counter® type particle characterization device of the present disclosure can be further adapted to automatically take a predetermined action when a blockage is detected. These actions can include stopping the run; attempting to remove the blockage and then stopping the run; or attempting to remove the blockage and then continuing the run. An advantage of electronically detecting a blockage is that the user of the device is not required to monitor each run by visually monitoring flow through the aperture, either directly through a magnified window or indirectly using a displayed image of the aperture. A further advantage is that electronic detection of a blockage based on multiple parameters characterizing the passage of particles through the aperture is more reliable than previous electronic methods based on a single parameter, particularly in cases of partial blockage of the aperture. A further advantage is that an action can be automatically taken when a blockage is detected, without need for user intervention. This action can include automatically attempting to remove the blockage and then continuing the run. In this way, a run can be completed while the device is unattended, even though a blockage of the aperture may occur during the run.

Figure 1:
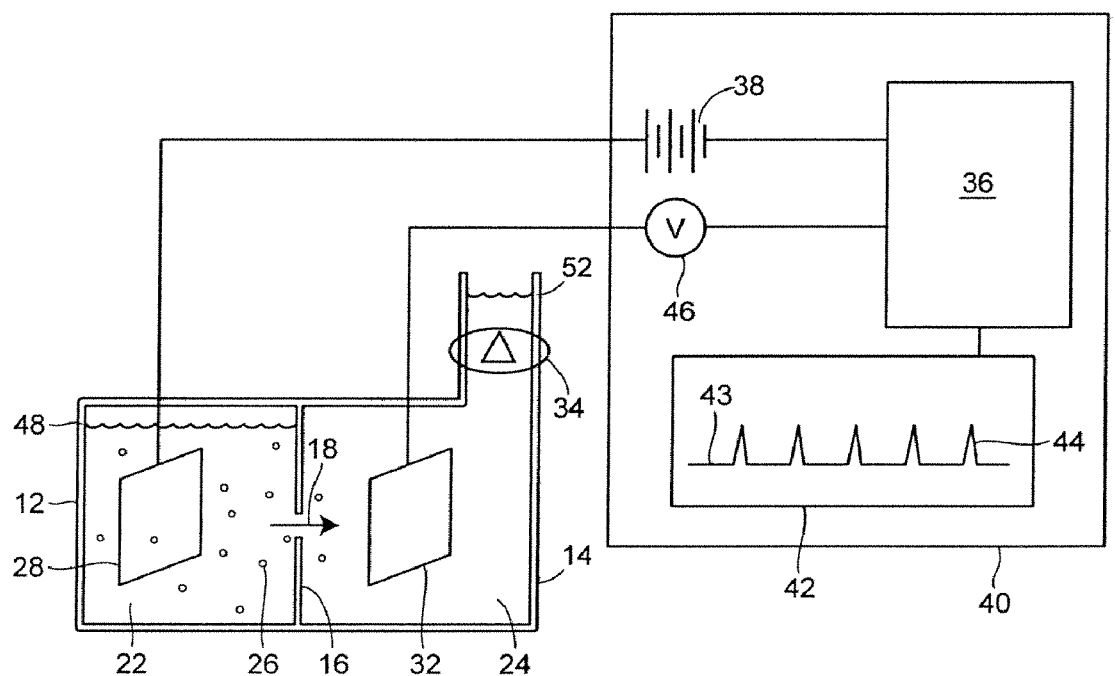
FIG. 1 illustrates an exemplary embodiment of a particle characterization device.

FIG. 1 illustrates one embodiment of a sample chamber 12 containing a liquid sample 22, and a collection chamber 14 containing an electrolyte solution 24. The liquid sample 22 in the sample chamber 12 comprises electrolyte and sample particles 26. The sample and collection chambers (12, 14) are separated by a wall 16 containing an aperture 18. A first electrode 28 and a second electrode 32 are disposed across the aperture 18 in the sample chamber 12 and the collection chamber 14, respectively. A voltage source 38 supplies voltage to the first and second electrodes (28, 32), creating an electrolytic current through the aperture 18. A pressure source 34 forces liquid sample 22 from the sample chamber 12, through the aperture 18, into the collection chamber 14. The aperture 18 is sized so that generally, only one sample particle 26 occupies the aperture 18 at any one time. Passage of uncharged sample particles 26 through the aperture 18 interferes with the current-induced flow of electrolyte through the aperture 18, causing a transient increase in the electrical resistance across the aperture 18. This transient increase in resistance is detected as a voltage pulse 44 by the voltage-pulse amplification and detection circuitry 36, which can be displayed by a processor 40 as an oscilloscope-like trace 43 on a display monitor 42. The presence of a voltage pulse 44 indicates the passage of typically a single sample particle 26 through the aperture 18, and the height of the pulse 44 is generally dependant on the size of the sample particle 26 passing through the aperture 18, since larger sample particles 26 tend to displace more electrolyte, causing a larger transient resistance across the aperture 18. In this way, the number and size of sample particles 26 in the liquid sample 22 can be determined.

The functioning of a Coulter Counter® type particle characterization device depends on the unobstructed passage of particles through the aperture 18. Sample particles 26 that are larger than the aperture 18, foreign particles, or an aggregation of sample particles 26 may partially or fully block the aperture 18. When such a blockage occurs, the blockage typically must be removed before particle characterization can continue.

Flow Rate

In the embodiment illustrated in FIG. 1, the pressure source 34 draws electrolyte solution 24 from the collection chamber 14, thereby drawing liquid sample 22, including sample particles 26, through the aperture 18 into the collection chamber 14. The pressure source 34 can be any suitable source, such as a flow pump, a vacuum pump, a positive displacement device such as a piston or syringe, or the force of gravity resulting from a difference in liquid levels between the sample chamber 12 and collection chamber 14. In another embodiment, the pressure source 34 is configured to push liquid sample 22 from the sample chamber 12 through the aperture 18 into the collection chamber 14.

Flow rate is the volume of liquid that passes through the aperture 18 during a given period of time. This volume of liquid can be calculated based on the change in liquid sample level 48 or electrolyte solution level 52 over the time period, or based on the change in weight of the sample chamber 12 or the collection chamber 14 over time, or by any other suitable means. In a preferred embodiment, a piston is used to draw electrolyte solution 24 from the collection chamber 14. The volume of liquid that passes through the aperture 18 over a given period of time can then be calculated based on the linear displacement of the piston over that time period. In another embodiment, flow rate is measured directly using a flow meter positioned to measure flow of the electrolyte solution 24 or of the liquid sample 22.

A blockage of the aperture 18 directly affects the flow rate through the aperture 18. A complete blockage brings the flow rate to essentially zero. A partial blockage reduces the flow rate to a percentage of the normal flow rate (without any blockage). A complete or partial blockage can therefore be detected by detecting a reduction in the flow rate through the aperture 18 during a particle-characterization run.

In some embodiments, a threshold value for flow rate is preselected before a particle-characterization run begins. This preselected threshold value can be a relative value, calculated as a percentage of the flow rate from a previous particle-characterization run, or it can be an absolute value, preselected by a user based on previous experience with the device, on simple preference, or it can be an absolute value that is an optimum or preferred value established by trial and error with the device. In some embodiments, the particle-characterization device is adapted to save the measured flow rates of previous runs, to present these values to the user prior to a subsequent run, and to allow the user to select the measured flow rate from a previous run as the basis of the threshold value for a subsequent run, where the threshold value is set as a percentage of an average or baseline value measured from that selected previous run. Typically, the previous run was run under similar conditions, such as using the same electrolyte composition, electric current, and size of aperture 18. Blockage of the aperture 18 is indicated when the measured flow-rate across the aperture 18 falls below the preselected threshold.

In other embodiments, the threshold flow rate value is set as a percentage of the flow rate calculated from the current run. In these embodiments, an average or baseline flow rate is calculated from the beginning of the run, and the preselected percentage of that average or baseline value is used as the threshold value for electronic detection of a blockage of the aperture 18 for the remainder of the run, where blockage is indicated when the measured flow rate across the aperture 18 falls below the calculated threshold value.

Aperture Resistance

In a Coulter Counter® type particle characterization device, voltage is applied to the first and second electrodes (28, 32) across the aperture 18 to maintain a constant current between the first and second electrodes (28, 32), dependent on the flow of electrolyte through the aperture 18. Complete or partial blockage of the aperture 18 can result in reduced flow of electrolyte through the aperture 18, leading to an increased calculated resistance across the aperture 18. In the embodiment illustrated in FIG. 1, the resistance across the aperture 18 is calculated from the voltage measured between the first and second electrodes (28, 32) by a voltage detector 46. The voltage detector 46 measures a steady-state voltage difference between the first and second electrodes (28, 32). The voltage-pulse amplification and detection circuitry 36 is a separate component, which generally measures the change in voltage between a steady-state level and the height of a transient pulse 44 as a particle passes through the aperture 18. This particle-associated pulse 44 is typically in the microvolt to millivolt range, compared to the blockage-associated change in steady-state voltage, which can be in the volt range, as shown, for example, in FIG. 5.

In some embodiments, a Coulter Counter® type particle characterization device is adapted to allow a user to preselect a threshold value for aperture resistance, where a measured value of aperture resistance that exceeds the threshold value is an indication of blockage of aperture 18. Just like flow rate disclosed above, the threshold value for aperture resistance can be set to an absolute value or to a relative value, the relative value calculated from either a previous (good) run or from the beginning of the run to which it is applied. Potential blockage of the aperture 18 is detected when the calculated resistance across the aperture 18 exceeds the preselected threshold value.

Particle Count Rate

Blockage of the aperture 18 of a Coulter Counter® type particle characterization device tends to decrease the rate that particles in the sample liquid pass through the aperture 18 and to affect the voltage pulses 44 of particles that do pass through, reducing the number of voltage pulses that can be distinguished by the device. Both of these effects lead to a decrease in the count rate measured by the device, where the count rate is the number of particle-associated voltage pulses detected per time period. In this way, detection of a reduced count rate is indicative of the presence of a complete or partial blockage of the aperture 18. In some embodiments, a Coulter Counter® type particle characterization device is adapted to allow a user to preselect a threshold value for particle count rate, where a measured value of particle count rate that falls below the preselected threshold is indicative of a blockage of the aperture 18. Just like flow rate and aperture resistance disclosed above, the threshold value for particle count rate can be set to an absolute value or to a relative value, the relative value calculated from either a previous (good) run or from the beginning of the run to which it is applied. Potential blockage of the aperture 18 is detected when the calculated particle count rate falls below the preselected threshold value.

Pulse Concentration

Pulse concentration can generally be defined as the percentage of the time that the voltage analyzed by a Coulter Counter® type particle characterization device is associated with a voltage pulse, typically corresponding to passage of a particle through the aperture 18. Blockage of the aperture 18 can lead to an increase in the calculated pulse concentration, due to increased voltage across the aperture 18 caused by the blockage. Therefore, detection of an increased pulse concentration during a particle characterization run can indicate the presence of a potential blockage of the aperture 18. In some embodiments, a Coulter Counter® type particle characterization device is adapted to allow a user to preselect a threshold value for pulse concentration, where a calculated value of pulse concentration that exceeds the preselected threshold during a run is indicative of blockage of the aperture 18. Just like flow rate, aperture resistance, and count rate disclosed above, the threshold value for pulse concentration can be set to an absolute value or to a relative value, the relative value calculated from either a previous (good) run or from the beginning of the run to which it is applied. Potential blockage of the aperture 18 is detected when the calculated pulse concentration exceeds the preselected threshold value.

Detection of Aperture Blockage Using Multiple Parameters

In some embodiments, a Coulter Counter® type particle characterization device is adapted to allow a user to preselect one or more parameters that will be used to identify an aperture blockage during a particle characterization run. A potential blockage of the aperture 18 will be detected if the measured value of any one of the preselected parameters exceeds a threshold value set by the user. In this way, a blockage can be detected that exceeds the threshold value of only one parameter, where such a blockage might otherwise be undetected if the threshold values of multiple parameters were required for blockage detection, or if a single parameter was chosen to detect all blockages. For example, one particular blockage may cause the threshold value for count rate only to be exceeded, while a second blockage may cause the threshold value of aperture resistance only to be exceeded. The particle characterization device of the present disclosure would be able to detect both blockages, while a device adapted to detect blockage using a single parameter would not.

The particle characterization device of the present disclosure may be further adapted to allow the user to accept a suggested default threshold value, or to alternatively choose a preferred value, that value being either an absolute value or a relative value, the relative value calculated from either the measured parameter values of a previous run, or calculated from the beginning of the present run. The device may be further adapted to allow a user to preselect a length of time that a threshold value is exceeded before an aperture blockage is detected. This allows transient blockages, lasting less than the preselected time period, to be ignored by the particle characterization device.

Figure 2:
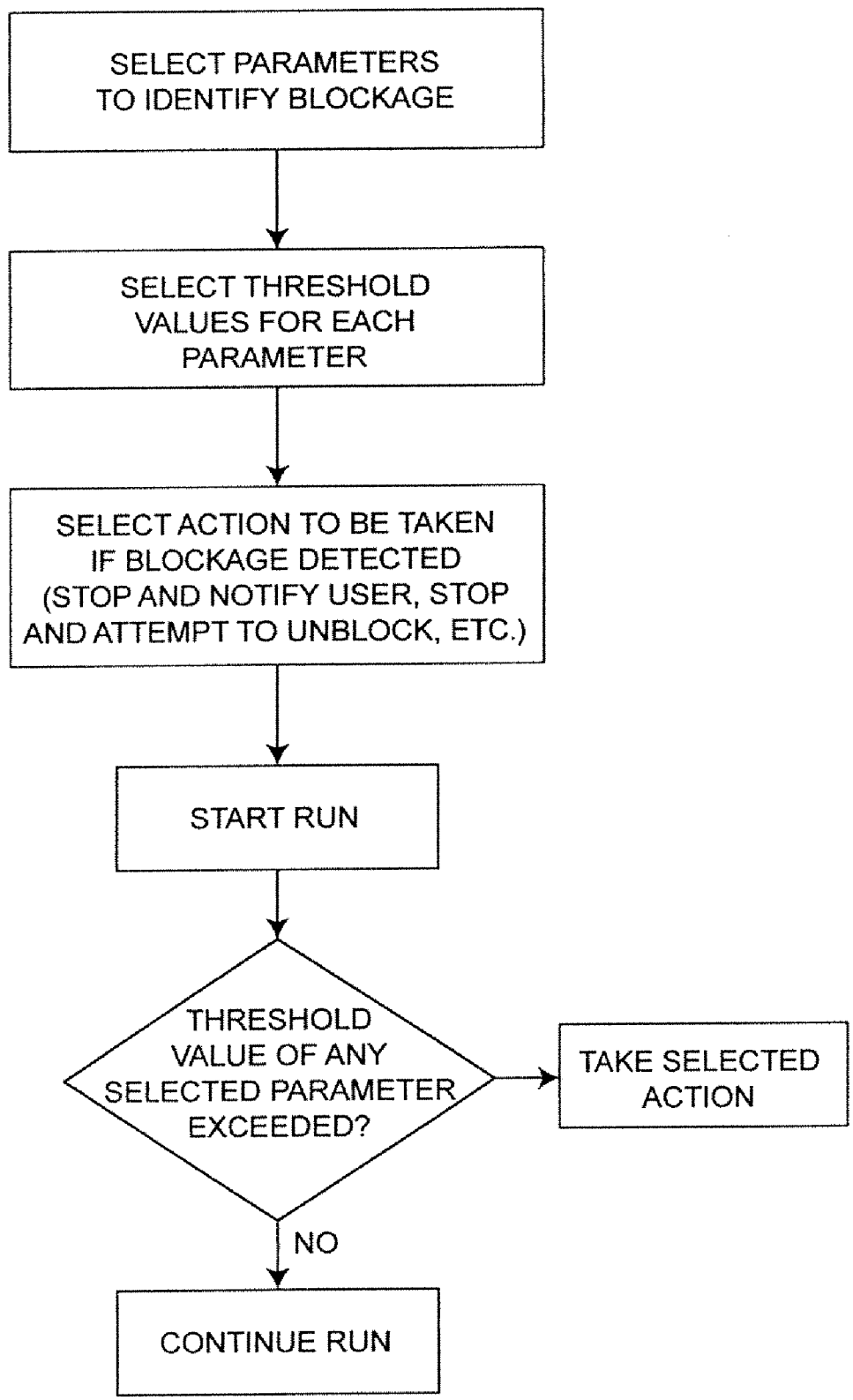
FIG. 2 illustrates an exemplary flowchart of a method of automatically detecting a blockage in an aperture of a particle characterization device.

FIG. 2 is a flow chart summarizing a particle characterization run using one embodiment of a particle characterization device of the present disclosure. In this embodiment, one or more parameters are selected by the user, and a threshold value for each of the selected parameters is chosen by the user, as well as the action that will be taken by the device if a blockage is detected. During the run, each selected parameter is monitored, and if the threshold value of any of the parameters is exceeded, the particle characterization device takes the preselected action.

Figure 3:
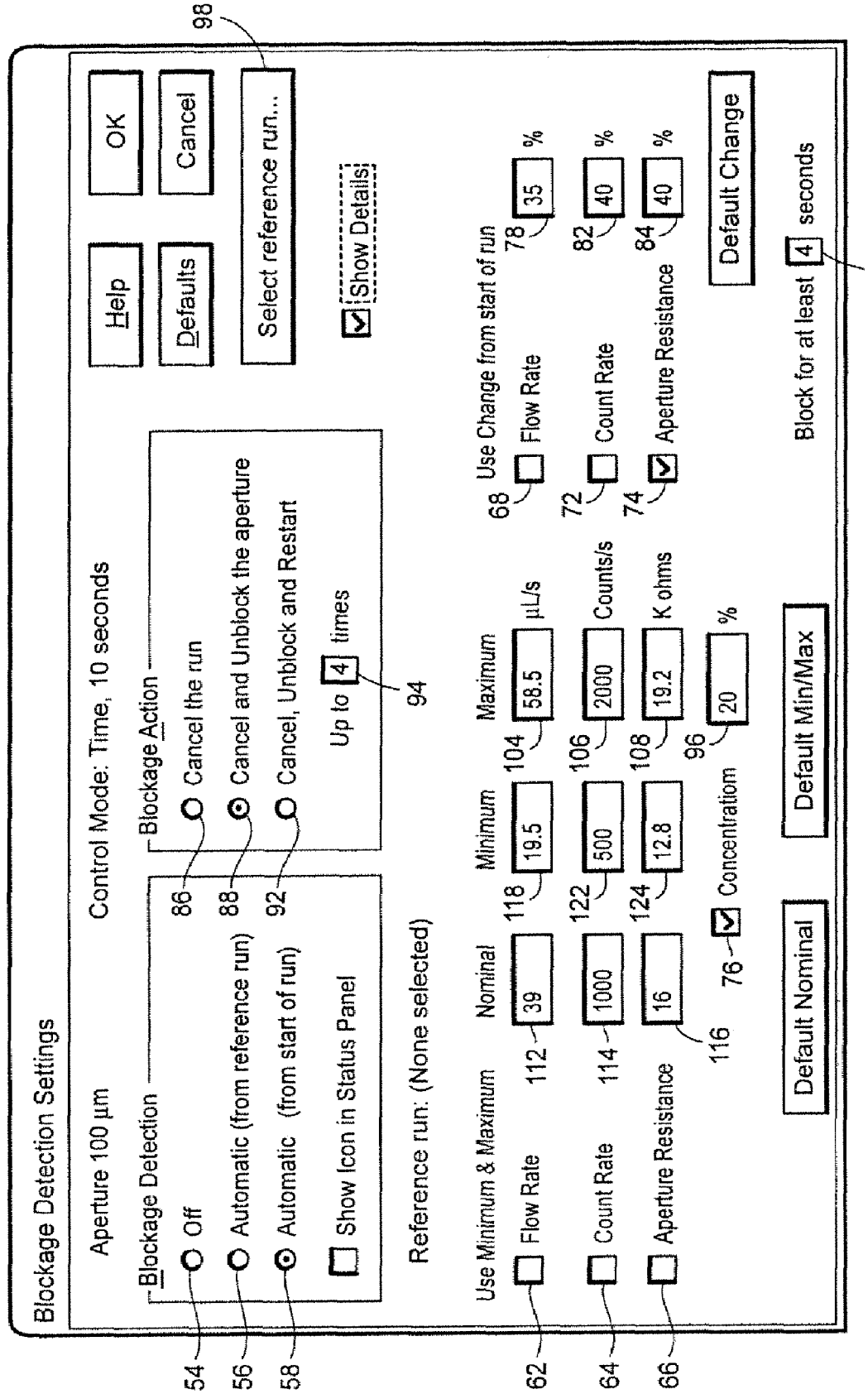
FIG. 3 illustrates an exemplary menu box displayed to a user of a particle characterization device.

FIG. 3 is an exemplary menu box that is displayed to a user in some embodiments of the disclosed particle characterization device. In these embodiments, a user can select whether or not to use automatic blockage detection for a particular run by selecting either radio button 54 to not use automatic blockage detection, or one of radio buttons 56 or 58 to use automatic blockage detection with threshold values based on a previous (reference) run or from the start of the current run, respectively. If radio button 56 is selected (to choose automatic detection based on a previous reference run), then the user may select which previous run to use by selecting menu button 98. After a user selects menu button 98, a second menu box appears, listing the previous runs and allowing the user to select one of them to establish the threshold parameter values for the present run. The second menu box also allows the user to select the percentage value that will be used to set an upper and lower threshold value for each parameter. Once the user selects the reference run and the percentage values, the device calculates upper and lower threshold values for each parameter by multiplying the nominal value from the reference run by the chosen percentage value, and displays the calculated upper threshold values in boxes 104, 106, and 108 for flow rate, count rate, and aperture resistance, respectively, and displays the lower threshold values in boxes 118, 122, and 124 for flow rate, count rate, and aperture resistance, respectively. The nominal values determined from the selected reference run are displayed in boxes 112, 114, and 116, for flow rate, count rate, and aperture resistance, respectively. The nominal values can be a baseline value calculated from the reference run, or they can be an average value calculated from the reference run. The reference run typically must be a previous run that used the same aperture size and the same type of electrolyte solution as the present run. The user can then choose which parameters to use for blockage detection by selecting check boxes 62, 64, 66, and/or 76 for flow rate, particle count rate, aperture resistance, or pulse concentration, respectively. If pulse concentration box 76 is selected, the user may enter a percentage value in box 96 to set the threshold value. For pulse concentration, a potential blockage is detected when the measured pulse concentration changes during a run by the percentage selected in box 96, (if check box 76 is selected), regardless of whether radio button 56 or 58 is selected.

In the illustrated embodiment of FIG. 3, if a user selects radio button 58 for automatic blockage detection using threshold values calculated from the start of the run, then the user can select which parameters to use for blockage detection by selecting check boxes 68, 72, 74, and/or 76 for flow rate, particle count rate, aperture resistance, and pulse concentration, respectively. The user can then enter the percentage values that will be used to calculate threshold values in boxes 78, 82, 84, and/or 96 for flow rate, particle count rate, aperture resistance, and pulse concentration, respectively.

In the illustrated embodiment, a user can set a time period for the threshold parameter values before aperture blockage is detected, by entering the desired time period into box 102. For example, if a user enters 4 (seconds) in box 102, then a potential blockage will be detected only if a measured value for a chosen parameter exceeds the threshold value for 4 seconds. This allows the particle characterization device to ignore transient anomalies or blockages and continue the run In some embodiments, default threshold values for parameters used for automatic blockage detection are presented to the user, specific for the aperture size and electrolyte solution chosen for the run by the user, so that a user can either accept the default values or enter a different value. In some embodiments, default threshold values for different combinations of aperture size and electrolyte solution are initially set by the manufacturer, but can be changed by the user.

Action Taken When Blockage Is Detected

In some embodiments, a Coulter Counter® type particle characterization device is adapted to detect aperture blockage based on the analysis of one or more preselected parameters. In other embodiments, the particle characterization device is further adapted to allow a user to preselect an action to be taken when aperture blockage is detected by the device. The preselected action can be, for example, to stop the analysis run, to stop the analysis run and attempt to remove the blockage, such as by reversing the flow of liquid through the aperture 18, or to attempt to remove the blockage and restart the run. In the later case, the device can be further adapted to allow the user to preselect the number of attempts the device makes to remove the blockage.

In the menu box of FIG. 3, a user can select the action that the device will take after blockage detection by selecting one of the radio buttons 86, 88, or 92, directing the device to either stop the run, to stop the run and attempt to remove the blockage, or to attempt to remove the blockage and restart the run, respectively. If the user chooses radio button 88 or 92, then the user can enter the number of attempts that the device will make to remove the blockage in box 94.

Aperture Blockage Detected by a Decreased Flow Rate During a Particle Characterization Run.

Figure 4:
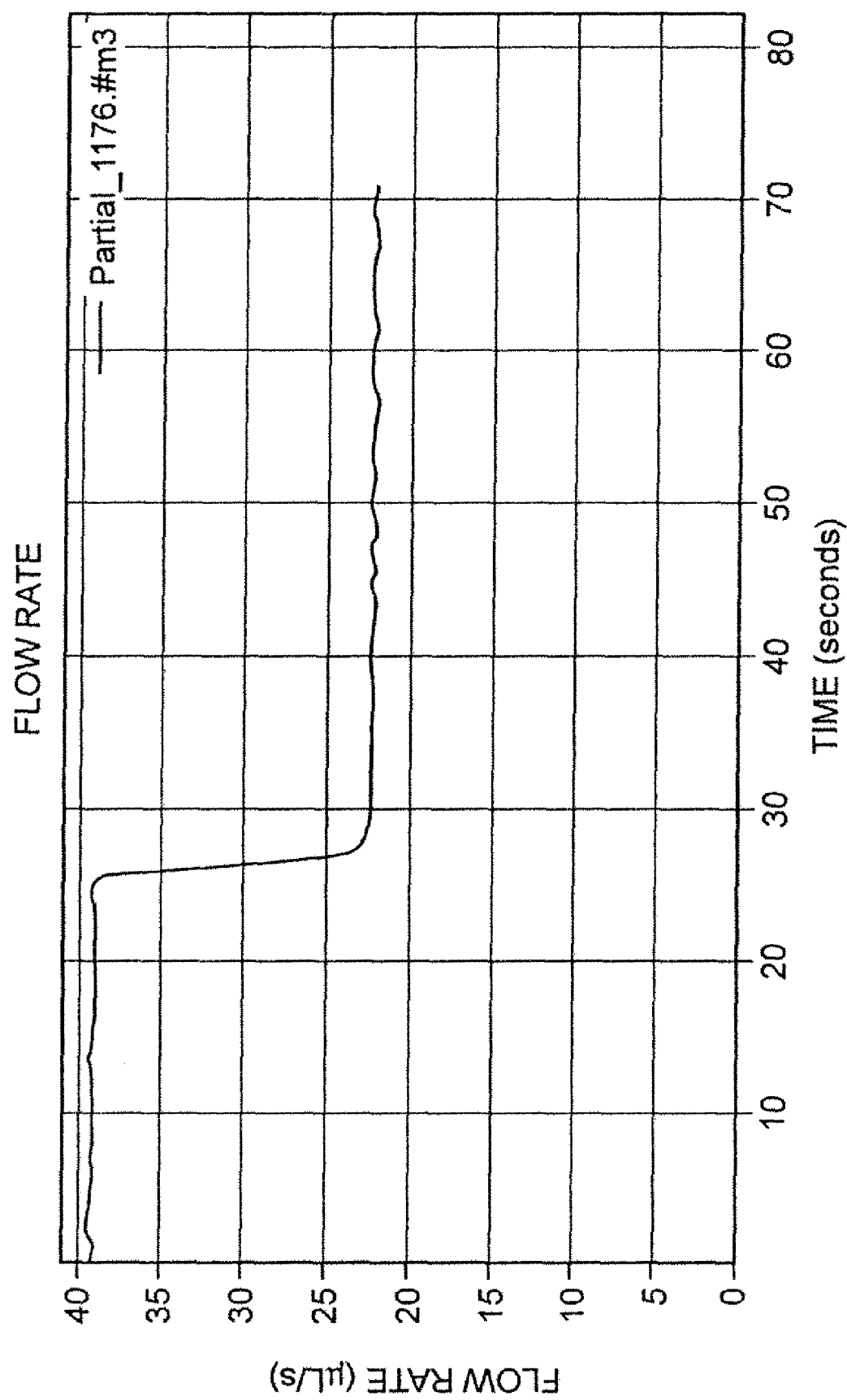
FIG. 4 illustrates a trace of flow rate measured when aperture blockage is detected by a decreased flow rate during a particle characterization run.

FIG. 4 displays a trace of the flow rate measured during a particle characterization run on a modified Multisizer™3 (Beckman Coulter; Fullerton, Calif.) particle characterization device. In this run, the electrolyte solution 24 was Isoton® II (Beckman Coulter; Fullerton, Calif.), and the liquid sample 22 comprised 10 μm PSL (polystyrene latex standard) sample particles 26 suspended in Isoton® II. A 100 μm aperture 18 was used, and the sample ran in volumetric mode (2000 μL) with current set to 800 μA and the gain at 4. Normal flow rate was 39 μL/sec. In this run, blockage of the aperture occurred approximately 25 seconds into the run. As shown in FIG. 4, this blockage resulted in a decrease in the measured flow rate, from approximately 39 μL/sec to approximately 22.5 μL/sec. The blockage remained for the remainder of the run, indicated by the constant reduced flow rate of approximately 22.5 μL/sec. The processor 40 in the disclosed device may thus be configured to detect a potential blockage of the aperture 18 during a particle characterization run by detecting a predetermined change in the flow rate through the aperture 18, wherein the predetermined change is a measured flow rate that is, for example, approximately 60% or less of the flow rate measured at the beginning of the particle characterization run.

Aperture Blockage Detected by an Increased Resistance Across the Aperture During a Particle Characterization Run.

Figure 5:
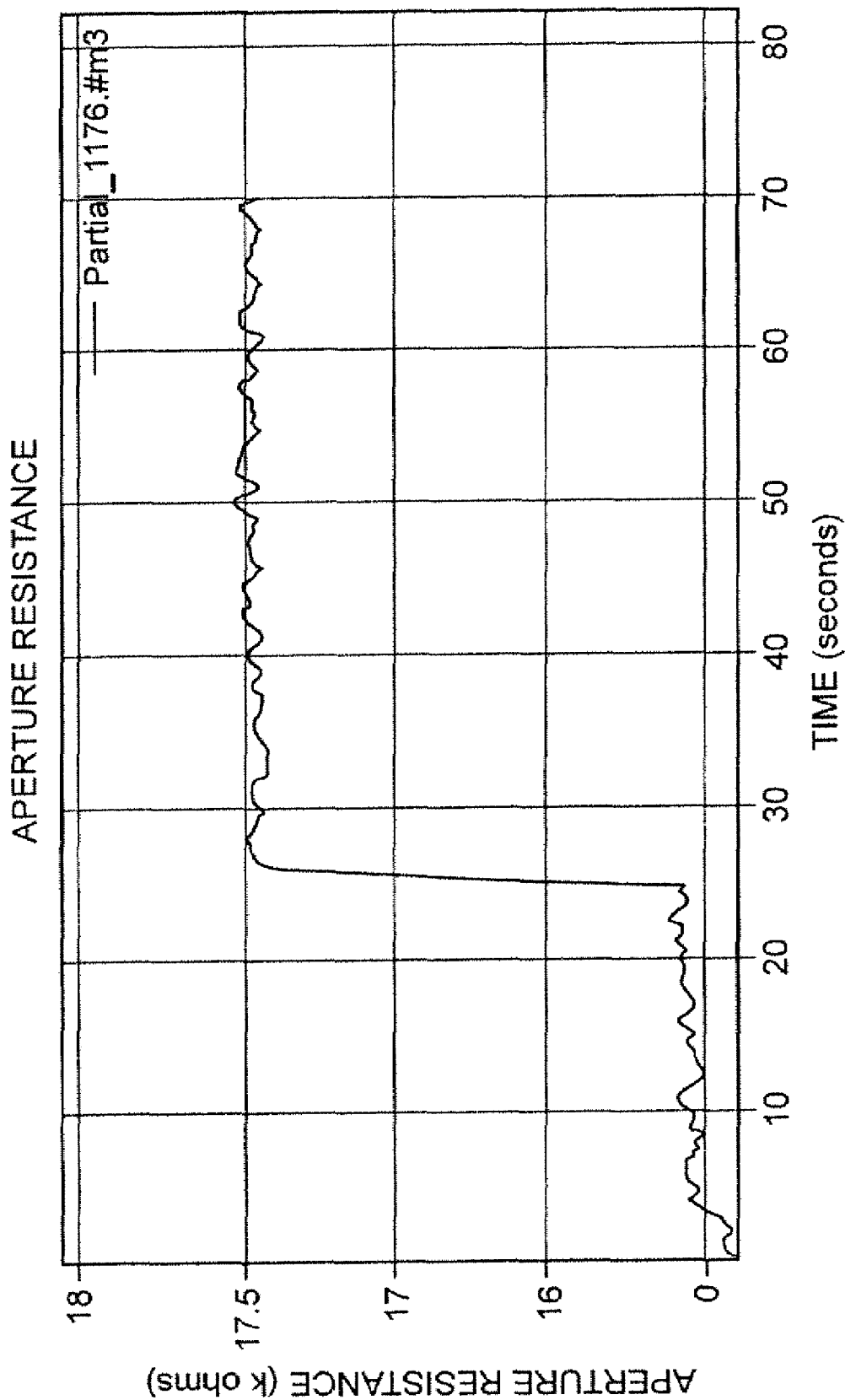
FIG. 5 illustrates a trace of measured resistance when aperture blockage is detected by an increased resistance across the aperture during the particle characterization run.

FIG. 5 is a trace of the measured resistance across the aperture 18 for the same particle characterization run as that shown if FIG. 4. In the run of FIG. 5, the steady-state voltage across the aperture 18 is approximately 16.1 k ohms at the beginning of the run, corresponding to a resistance across the aperture 18 of approximately 12.9 volts, calculated using Ohm's law with a constant current of 800 μA. At approximately 25 seconds into the run, a blockage of the aperture 18 leads to an increase in the calculated resistance across the aperture 18 to approximately 17.4 k ohms, corresponding to an increase to approximately 13.9 volts. The aperture resistance remained at approximately 17.4 k ohms for the remainder of the run, indicating that the aperture 18 remained blocked.

Aperture Blockage Detected by a Decreased Count Rate During a Particle Characterization Run.

Figure 6:
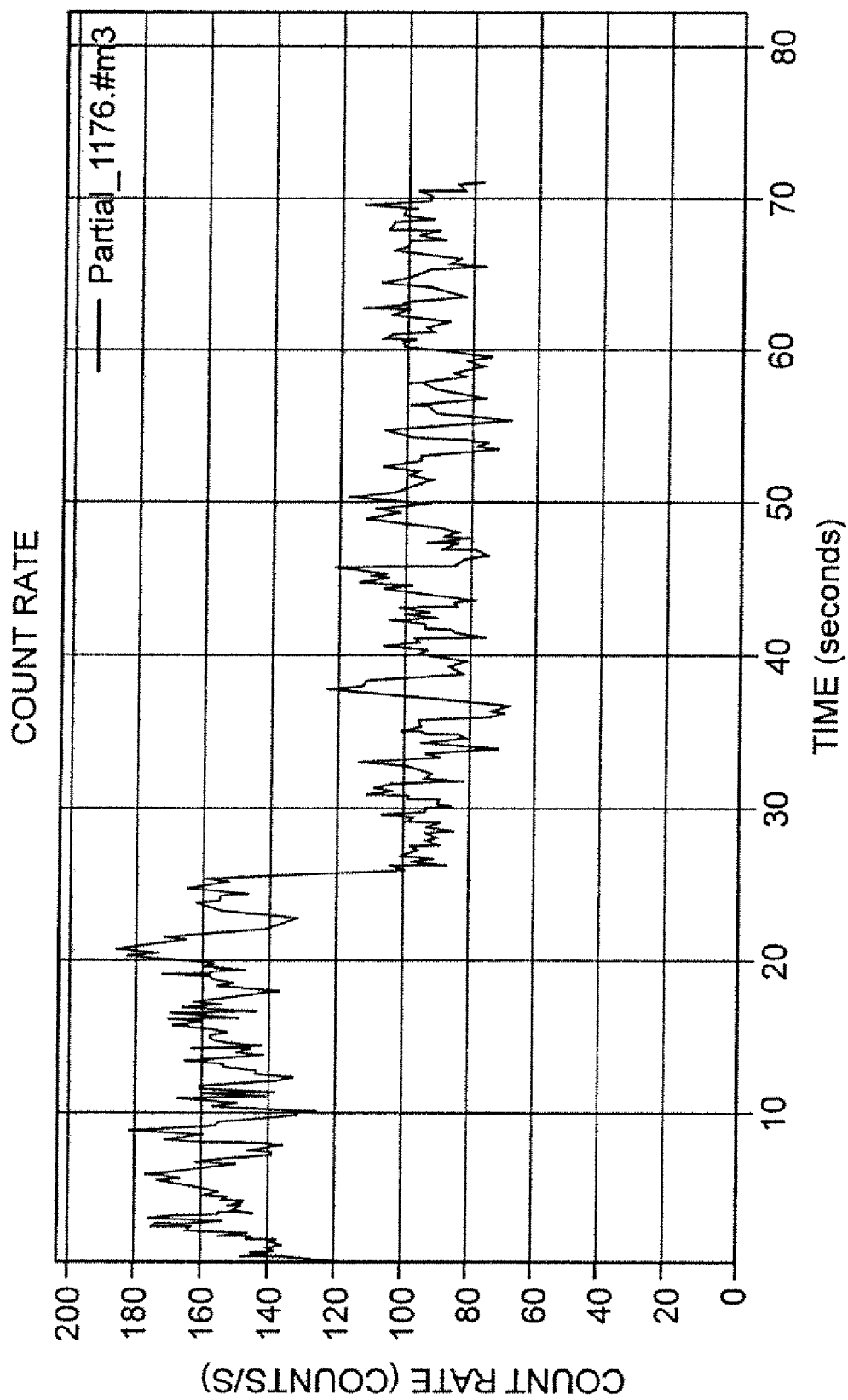
FIG. 6 illustrates a trace of measured particle count rate when aperture blockage is detected by a decreased count rate during the particle characterization run.

FIG. 6 is a trace of measured particle count rate for the same particle characterization run as that shown in FIGS. 4 and 5. The count rate averages approximately 150 counts/sec for the beginning of the run, then decreases to an average of approximately 90 counts/sec at approximately 25 seconds into the run, when the aperture became blocked. The count rate remained at approximately 90 counts/sec for the remainder of the run, indicating that the aperture 18 remained blocked.

Aperture Blockage Detected by an Increased Pulse Concentration During a Particle Characterization Run.

Figure 7:
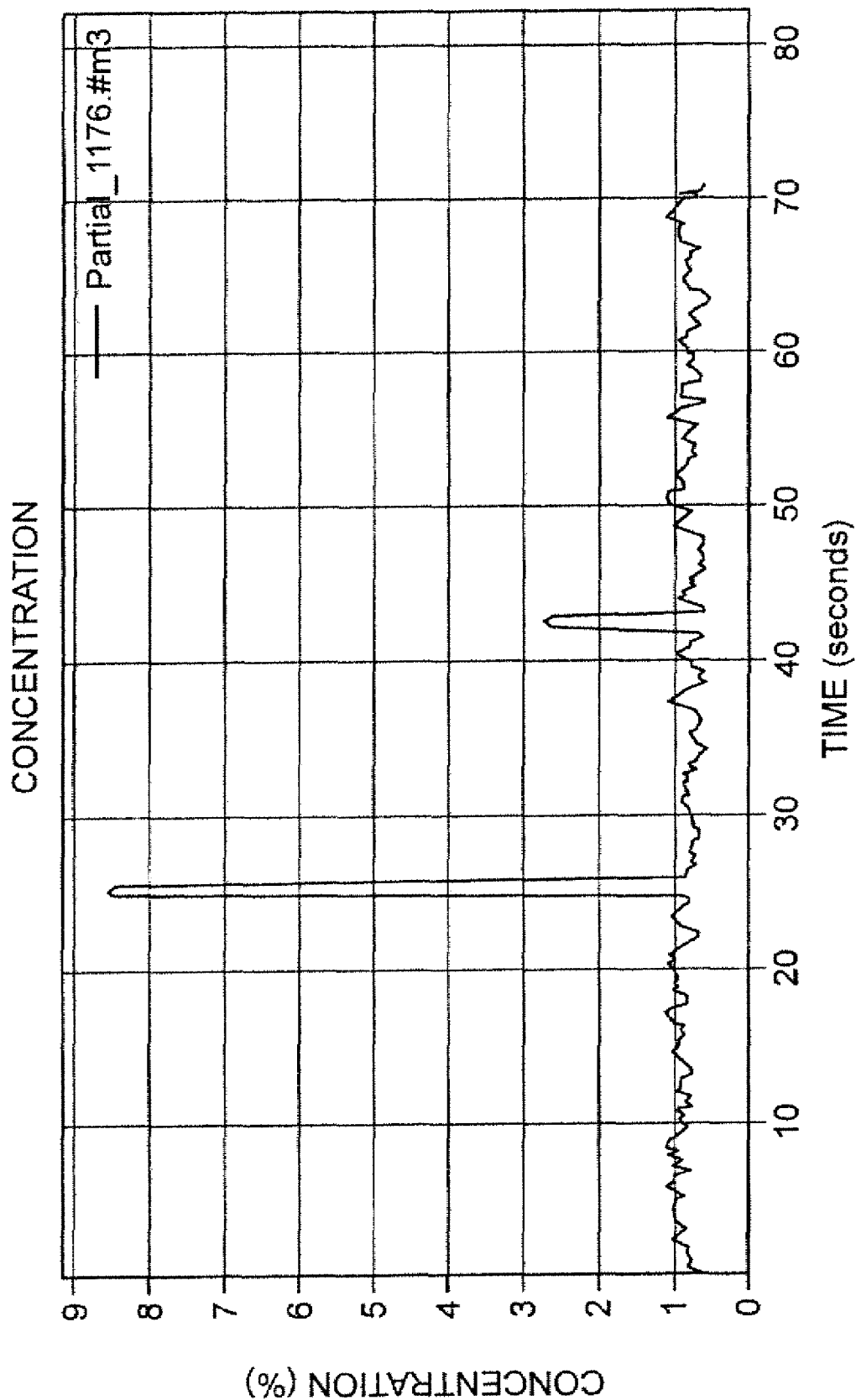
FIG. 7 illustrates a trace of calculated pulse concentration when aperture blockage is detected by an increased pulse concentration during the particle characterization run.

FIG. 7 is a trace of calculated pulse concentration for the same particle characterization run as that shown in FIGS. 4-6. The count rate spiked from approximately 0.9% to approximately 8.5% at approximately 25 seconds into the run, indicating blockage of the aperture 18.

Figure 8:
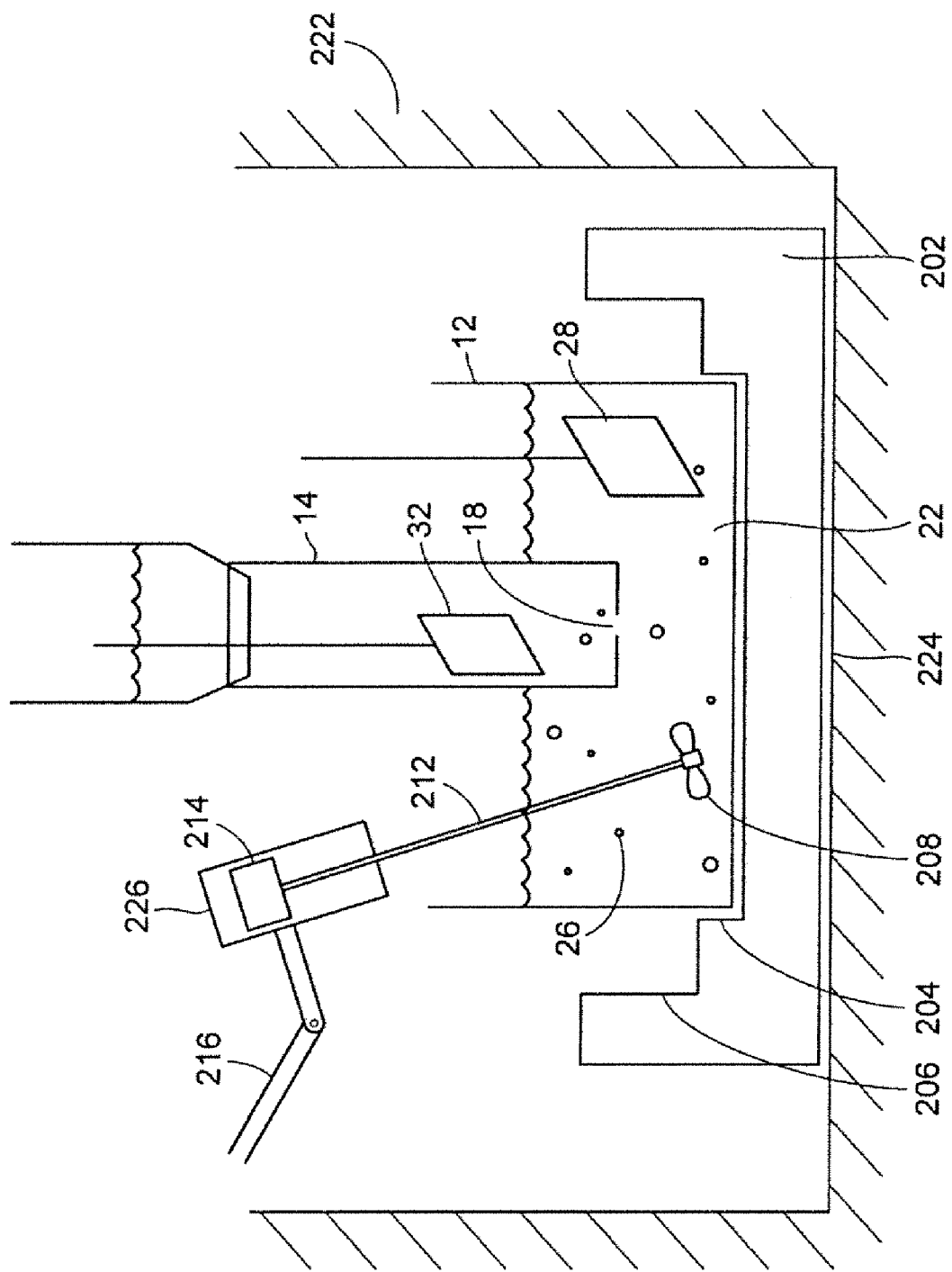
FIG. 8 illustrates another embodiment of a Coulter Counter® type particle characterization device.

FIG. 8 illustrates an embodiment of a Coulter Counter® type particle characterization device of the present disclosure, comprising a housing 222 with a base 224 and a stage 202 on the base for holding the sample chamber 12 in position. Different-sized collection chambers 14 and different-sized sample chambers 12 can be used on the particle characterization device. The stage 202 is configured to hold the different-sized sample chambers 12 at different positions relative to the base 224. In the illustrated embodiment, a first sample chamber 12 fits into a first guide 204 of the stage 202. A second guide 206 is configured to hold a second-sized sample chamber 12 at a position that is different than the position of the first sample chamber. This arrangement allows different-sized collection chambers 14 to be used with corresponding different-sized sample chambers 12, with the first and second guides 204 and 206 configured to position and hold the respective sample chamber 12 at the appropriate position relative to the corresponding collection chamber 14. In another embodiment, the base 224 is movable, with the position of the base 224 controlled by the processor 40. The processor 40 positions the base 224 to place the selected sample chamber 12 at an appropriate position relative to the selected collection chamber 14, based on information entered by a user regarding the type and/or size of sample chamber 12 and collection chamber 14 being used on the device. In another embodiment, the type and/or size of sample chamber 12 and collection chamber 14 is encoded in an indicia or barcode on the sample chamber 12 and collection chamber 14, and an indicia reader or barcode reader is coupled to the processor 40 to decode the indicia or barcode and to input the type and/or size information of the sample chamber 12 and the collection chamber 14 into the processor 40.

A first and second guide 204 and 206 are disclosed in the illustrated embodiment. A device of the present disclosure can have more than 2 guides to accommodate more than 2 sizes of sample chamber 12 and collection chamber 14. The guides 204 and 206 ensure that a sample chamber 12 will be in an optimum and consistent position relative to the collection chamber 14 for more consistent particle characterization results. The guides 204 and 206 also ensure that the sample chamber 12 will not come into contact or crash into the collection chamber 14 or the first electrode 28.

A stirrer 208 in the sample liquid 22 stirs the sample liquid 22 during the particle characterization run to maintain a uniform suspension of sample particles 26 in the liquid sample 22. In the illustrated embodiment, the stirrer 208 is connected to a shaft 212 that is rotated by a motor 214 in a stirrer base 226. A movable stirrer arm 216 connects the stirrer base 226 to the device housing 222. The stirrer arm 216 is movable to position the stirrer 208 at a desired position in the sample chamber 12 relative to the collection chamber 14 and aperture 18. In a preferred embodiment, the stirrer arm is coupled to the processor 40 so that the position of the stirrer arm 216 is controlled by the processor 40. The processor 40 positions the stirrer at an appropriate position based on the information regarding the size and/or type of sample chamber 12 and collection chamber 14 that is input into the processor 40. That information can be input by a user, or it can be input by an indicia or barcode scanning device coupled to the processor 40 that scans an indicia or barcode on the sample chamber 12 and collection chamber 14 encoding the size and/or type information. In one embodiment, the stirrer motor 214 is coupled to the processor 40 so that the processor 40 controls the speed and direction of rotation of the stirrer 208. The speed and direction of rotation of the stirrer 208 can be selected by a user of the device. A preferred speed and direction of rotation can be presented by the processor 40 to a user, based on the composition and viscosity of the electrolyte solution 24 used for the particle characterization run and on the size and/or type of sample chamber 12 and collection chamber 14 used on the device. Which electrolyte solution 24 is being used on the particle characterization device can be input into processor 40 by a user or by an indicia or barcode scanning device coupled to the processor 40 that scans an indicia or barcode on the electrolyte-solution container encoding information on the composition of the electrolyte solution 24. The indicia or barcode on the electrolyte-solution container can also encode the lot number and expiration date of the electrolyte solution 24.

In some embodiments, the processor 40 records stirrer 208 position, speed, and direction of rotation, including adjustments made during an analysis run, to allow a user to reproduce analysis results.

An apparatus for characterizing particles suspended in a liquid sample containing electrolyte is disclosed that includes (a) a sample chamber for holding the liquid sample and a collection chamber for holding an electrolyte solution, the sample and collection chambers separated by a wall, (b) an aperture in the wall for passage of particles between the sample chamber and collection chamber, (c) a pair of electrodes disposed on opposite sides of the aperture for inducing an electric current through the aperture, (d) a pressure source for drawing the liquid sample from the sample chamber into the collection chamber through the aperture, and (e) a processor for measuring a signal representative of electrical resistance variation between the electrodes to enable determination of the size of the particle within the liquid passing through the aperture, wherein the processor is adapted to detect a potential blockage of the aperture by detecting a predetermined change in one or more parameters characterizing the flow of particles through the aperture, wherein at least one of the one or more parameters is selected from the group consisting of flow rate, count rate, pulse concentration, and aperture resistance.

The predetermined change may be a measured value that exceeds a predetermined threshold value for any of the one or more parameters. The predetermined threshold value for at least one of the one or more parameters may be selected by a user of the apparatus. The predetermined threshold value for at least one of the one or more parameters may also be an absolute value. Alternatively, the predetermined threshold value for at least one of the one or more parameters may be a relative value, dependant on the measured values from a previous run. The predetermined threshold value for at least one of the one or more parameters is a relative value, dependant on the measured values from the beginning of the present run.

The processor may be adapted to detect the potential blockage of the aperture if the threshold value is exceeded for a preselected length of time. Also, the one or more parameters may be preselected by a user of the apparatus. The processor may be further adapted to direct a predetermined action when potential blockage of the aperture is detected. The predetermined action may be, for example, an attempt to remove the blockage. The pressure source that draws the liquid sample into the collection chamber may be a piston, and the flow-rate of liquid sample through the aperture may determined by monitoring the displacement of the piston.

Although the forgoing text sets forth a detailed description of numerous different embodiments, it should be understood that the scope of the patent is defined by the words of the claims set forth at the end of this patent. The detailed description is to be construed as exemplary only and does not describe every possible embodiment because describing every possible embodiment would be impractical, if not impossible. Numerous alternative embodiments could be implemented, using either current technology or technology developed after the filing date of this patent, which would still fall within the scope of the claims.

Thus, many modifications and variations may be made in the techniques and structures described and illustrated herein without departing from the spirit and scope of the present claims. Accordingly, it should be understood that the methods and apparatus described herein are illustrative only and are not limiting upon the scope of the claims.

We claim:

1. An apparatus for characterizing particles suspended in a liquid sample containing electrolyte, the apparatus comprising:
    (a) a sample chamber for holding the liquid sample and a collection chamber for holding an electrolyte solution, the sample and collection chambers separated by a wall;
    (b) an aperture in the wall for passage of particles between the sample chamber and collection chamber;
    (c) a pair of electrodes disposed on opposite sides of the aperture for inducing an electric current through the aperture;
    (d) a pressure source for drawing the liquid sample from the sample chamber into the collection chamber through the aperture; and
    (e) a processor for measuring a signal representative of electrical resistance variation between the electrodes to enable determination of the size of a particle within the liquid passing through the aperture, wherein the processor is adapted to detect a potential blockage of the aperture by detecting a predetermined change in one or more parameters characterizing a flow of particles through the aperture, wherein at least one of the one or more parameters is selected from the group consisting of flow rate, count rate, pulse concentration, and steady-state aperture resistance wherein the processor is further adapted to direct a preselected action when potential blockage of the aperture is detected, wherein the preselected action is preselected by a user of the apparatus from a choice of two or more actions.

2. The apparatus of claim 1, wherein the predetermined change is a measured value that exceeds a predetermined threshold value for any of the one or more parameters, and wherein the predetermined threshold value is a value that is predetermined by a user of the apparatus.

3. The apparatus of claim 1, wherein the predetermined change is a measured value that exceeds a predetermined threshold value for any of the one or more parameters, and wherein the predetermined threshold value for at least one of the one or more parameters is a relative value dependent on a measured value from a previous particle characterization run.

4. The apparatus of claim 1, wherein the predetermined change is a measured value that exceeds a predetermined threshold value for any of the one or more parameters, and wherein the predetermined threshold value for at least one of the one or more parameters is a relative value dependent on a measured value from the present particle characterization run.

5. The apparatus of claim 1, wherein the predetermined change is a measured value that exceeds a predetermined threshold value for a predetermined length of time.

6. The apparatus of claim 5, wherein the predetermined length of time is predetermined by a user of the apparatus.

7. The apparatus of claim 1, wherein the pressure source is a piston, and wherein the processor is configured to determine a flow rate of liquid sample through the aperture by monitoring the displacement of the piston.

8. The apparatus of claim 1, wherein the processor is adapted to simultaneously monitor flow rate, count rate, pulse concentration, and steady-state aperture resistance.

9. The apparatus of claim 1, wherein the processor is adapted to detect a potential blockage of the aperture during a particle characterization run by detecting a predetermined change in the flow rate through the aperture, wherein the predetermined change is a measured flow rate that is approximately 60% or less of the flow rate measured at the beginning of the particle characterization run.

10. An apparatus for characterizing particles suspended in a liquid sample containing electrolyte, the apparatus comprising:
    (a) a sample chamber configured to hold the liquid sample and a collection chamber configured to hold an electrolyte solution, the sample and collection chambers separated by a wall;
    (b) an aperture in the wall to allow passage of particles between the sample chamber and the collection chamber;
    (c) a pair of electrodes disposed on opposite sides of the aperture configured to induce an electric current through the aperture;
    (d) a pressure source configured to force the liquid sample to pass from the sample chamber into the collection chamber through the aperture; and
    (e) a processor configured to measure a signal representative of electric resistance variation between the electrodes to enable determination of the size of the particle within the liquid passing through the aperture, wherein the processor is adapted to monitor two or more parameters characterizing a flow of particles through the aperture, wherein the processor is further adapted to detect a potential blockage of the aperture by detecting a predetermined change in any one of the two or more parameters, and the processor is further adapted to direct a preselected action when potential blockage of the aperture is detected, wherein the preselected action is preselected by a user of the apparatus from a choice of two or more actions.

11. The apparatus of claim 10, wherein at least one of the two or more parameters is from the group of flow rate, count rate, pulse concentration, and steady-state aperture resistance.

12. The apparatus of claim 10, wherein the processor is adapted to simultaneously monitor flow rate through the aperture and steady-state resistance across the aperture.

13. The apparatus of claim 10, wherein the processor is adapted to monitor steady-state resistance across the aperture, and wherein the processor is adapted to detect a potential blockage of the aperture by detecting a change in the steady-state resistance across the aperture that leads to a change in voltage across the aperture of approximately 1 volt or more.

14. The apparatus of claim 10, wherein the processor is adapted to monitor particle count rate during a particle characterization run, and wherein the processor is adapted to detect a potential blockage of the aperture by detecting a measured particle count rate during the run that is approximately 60% or less of the particle count rate measured during the beginning of the run.

15. The apparatus of claim 10, wherein the predetermined change is a measured value that exceeds a predetermined threshold value, wherein the predetermined threshold value is a predetermined percentage of a measured value from the beginning of the present particle characterization run.

16. A method for automatically detecting a potential blockage in an aperture of a Coulter-type particle-characterization device, the method embodied in a set of machine-readable instructions executed on a processor, the method comprising:
  (a) monitoring one or more parameters characterizing a flow of particles through the aperture, wherein at least one of the one or more parameters is selected from the group consisting of flow rate, count rate, pulse concentration, and steady-state aperture resistance;
  (b) detecting a predetermined change in one of the one or more parameters, wherein the predetermined change is a measured value that exceeds a predetermined threshold value indicative of a blockage of the aperture;
  (c) identifying a potential blockage of the aperture when the measured value exceeds the predetermined threshold value; and
  (d) taking a predetermined action when a potential blockage of the aperture is identified, wherein the predetermined action of (d) is preselected by a user of the apparatus from a choice of two or more actions.

17. The method of claim 16, wherein one or more parameters are monitored in (a), wherein at least one of the one or more parameters is selected from the group consisting of count rate, pulse concentration, and steady-state aperture resistance, and wherein a potential blockage of the aperture is identified in (c) when the measured value for any one of the one or more monitored parameters exceeds the predetermined threshold value for that parameter.

18. The method of claim 16, wherein the steady state resistance across the aperture is monitored in (a), and wherein a potential blockage of the aperture is identified in (c) when the measured steady-state resistance across the aperture exceeds a preselected percentage of the measured steady-state resistance across the aperture from the beginning of the particle characterization run.

* * * * *